US008444659B2

(12) United States Patent
Stone et al.

(10) Patent No.: US 8,444,659 B2

(45) Date of Patent: May 21, 2013

(54) METHOD AND APPARATUS FOR PASSING A SUTURE THROUGH TISSUE

(75) Inventors: Kevin T. Stone, Winona Lake, IN (US); Troy M. Walters, Plymouth, IN (US)

(73) Assignee: Biomet Sports Medicine, LLC, Warsaw, IN (US)

( * ) Notice: Subject to any disclaimer, the term of this patent is extended or adjusted under 35 U.S.C. 154(b) by 262 days.

(21) Appl. No.: 12/777,704

(22) Filed: May 11, 2010

(65) Prior Publication Data

US 2010/0222791 A1 Sep. 2, 2010

Related U.S. Application Data

(62) Division of application No. 10/984,608, filed on Nov. 9, 2004, now Pat. No. 7,722,630.

(51) Int. Cl.
*A61B 17/04* (2006.01)

(52) U.S. Cl.
USPC .......................................... 606/144; 606/139

(58) Field of Classification Search
USPC ................................................ 606/144, 139
See application file for complete search history.

(56) References Cited

U.S. PATENT DOCUMENTS 5,522,820 A 6/1996 Caspari et al.
5,707,379 A 1/1998 Fleenor et al.
5,730,747 A 3/1998 Ek et al.
5,935,149 A 8/1999 Ek
6,051,006 A 4/2000 Shluzas et al.
6,605,096 B1 8/2003 Ritchart
6,770,084 B1 8/2004 Bain et al.
7,722,630 B1 5/2010 Stone et al.
2003/0078599 A1 4/2003 O'Quinn et al.
2003/0083695 A1 5/2003 Morris et al.

*Primary Examiner* — Gregory Anderson
(74) *Attorney, Agent, or Firm* — Harness, Dickey

(57) ABSTRACT

An apparatus and method for passing a suture through tissue includes a first jaw member having a retaining structure to support a portion of the suture proximate a first surface of the tissue. A second jaw member is associated with the first jaw member. The second jaw member is selectively configurable in a first configuration to perform a first stitch or in a second configuration to perform a second stitch.

24 Claims, 7 Drawing Sheets

84 88 14 60 22 82 48 76 50 10 62 52 42 20 44 40 38 12 18 30 98 100 24 26 $D_2$ $D_1$ 204
240
260
242
262
280
T
218
220
270
272
216
214
30
230

256
258

234
236
238
250
252
224
202

METHOD AND APPARATUS FOR PASSING A SUTURE THROUGH TISSUE

CROSS-REFERENCE TO RELATED APPLICATIONS

This application is a divisional of U.S. patent application Ser. No. 10/984,608 now U.S. Pat. No. 7,722,630 filed on Nov. 9, 2004. The entire disclosure of the above application is incorporated herein by reference.

FIELD OF THE INVENTION

The present invention relates to suturing and more particularly to a method and apparatus for passing a suture through tissue.

BACKGROUND OF THE INVENTION

In some instances during a surgical procedure it is necessary to suture tissue such as to join a wound in the tissue or join adjacent tissues. A number of surgical instruments are available for facilitating the suturing of tissue. In some instruments a pair of jaw structures are provided for passing a needle through the tissue and subsequently passing a suture through the needle to communicate the suture from one surface of tissue to another. In other configurations, a needle having a suture attached is passed from a first jaw to a second jaw through the tissue.

Sometimes different stitch patterns are required from one surgical procedure to another. For example, depending on the surgical procedure to be performed a single or mattress stitch may be desired. As a result, a surgeon may be required to utilize distinct instruments as dictated by the desired stitch pattern. While current surgical instruments have been shown to be adequate for the intended purpose, a need exists in the art to provide a simpler and more efficient instrument for performing a suturing procedure.

SUMMARY OF THE INVENTION

An apparatus and method for passing a suture through tissue includes a first jaw member having a retaining structure to support a portion of the suture proximate a first surface of the tissue. A second jaw member is associated with the first jaw member. The second jaw member is selectively configurable in a first configuration to perform a first stitch or in a second configuration to perform a second stitch.

According to other features, the second jaw member is operable to employ at least one of a first needle and a second needle. The second jaw member includes a plurality of second jaw members. One of the plurality of second jaw members includes the first needle to perform the first stitch and another of the plurality of jaw members includes the first and second needles to perform the second stitch. The first and the second needle are disposed at a distal end of the second jaw member for piercing through the tissue from a second surface to the first surface. The first and second needle defines a hook for capturing the supported portion of the suture upon actuation of one of the first and second jaw members in a first direction and drawing a portion of the suture from the first surface of the tissue, through the tissue and to the second surface of the tissue upon actuation of one of the first and second jaw members in a second direction.

According to other features, the first and second jaw members are pivotally coupled. The first jaw includes a body portion having the retaining structure thereon. The retaining structure defines a groove for locating a portion of the suture thereat. The body portion includes a distal portion and a proximal portion. The proximal portion is coupled to the second jaw at a pivot point. The distal portion and the proximal portion define an upper face opposing the second jaw, a lower face and a sidewall extending between the upper face and the lower face, the sidewall having the groove therein.

A method for passing a suture through tissue using an instrument having first and second jaw members includes locating the tissue between the first and second jaw member. One of the first and second jaw members is advanced through the tissue in a first direction toward the tissue whereby the needle advances through the tissue creating a single pierced hole in the tissue. One of the first and second jaw members are advanced in a second direction whereby the needle captures the supported portion of the suture and draws the suture through the pierced hole in the tissue.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

DETAILED DESCRIPTION OF THE PREFERRED EMBODIMENTS

The following description of the embodiment(s) is merely exemplary in nature and is in no way intended to limit the invention, its application, or uses.

Figure 4:
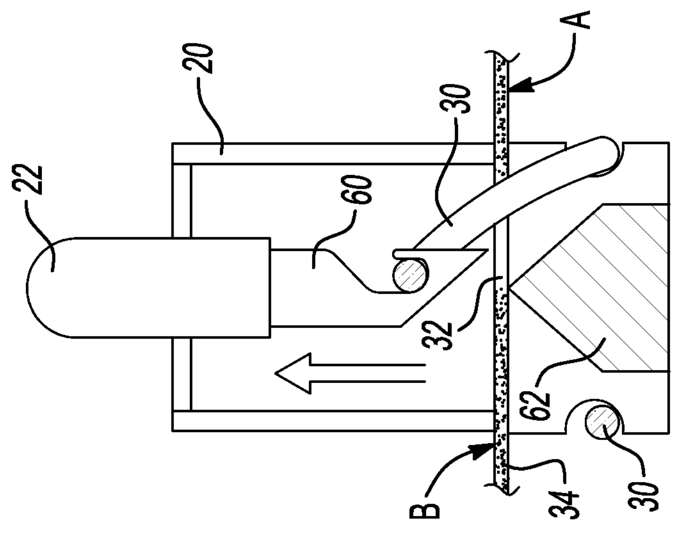
FIG. 4 is a cross-sectional view of the jaw portion of FIG. 3 shown with a captured portion of suture during retraction from the tissue.

With initial reference to FIGS. 1-4, an apparatus for passing a suture through tissue is shown and generally identified at reference 10. The apparatus 10 generally includes a longitudinal shaft 12 extending between a jaw end 14 and a handle end 18. The jaw end 14 includes a first and second jaw member 20 and 22 respectively. The handle end 18 includes a first and second handle member 24 and 26 respectively. As will be described in greater detail, relative actuation of the handles 24 and 26 causes relative actuation between the first and second jaw members 20 and 22. The first and second jaw members 20 and 22 cooperate to pass a length of suture 30 through a pierced hole 32 formed in the tissue 34 (FIG. 4).

The longitudinal shaft 12 includes a hollow tubular portion 38 having a rod (not shown) positioned therein for linear actuation upon movement of the second handle 26 toward the first handle 24. A distal end of the rod cooperates with the second jaw member 22 to influence pivotal movement of the second jaw member 22 about a pivot joint 40. It is appreciated that other mechanical configurations may be employed for imparting pivotal movement between the first and second jaw members 20 and 22. Various other handle configurations may also be employed.

Figure 1:
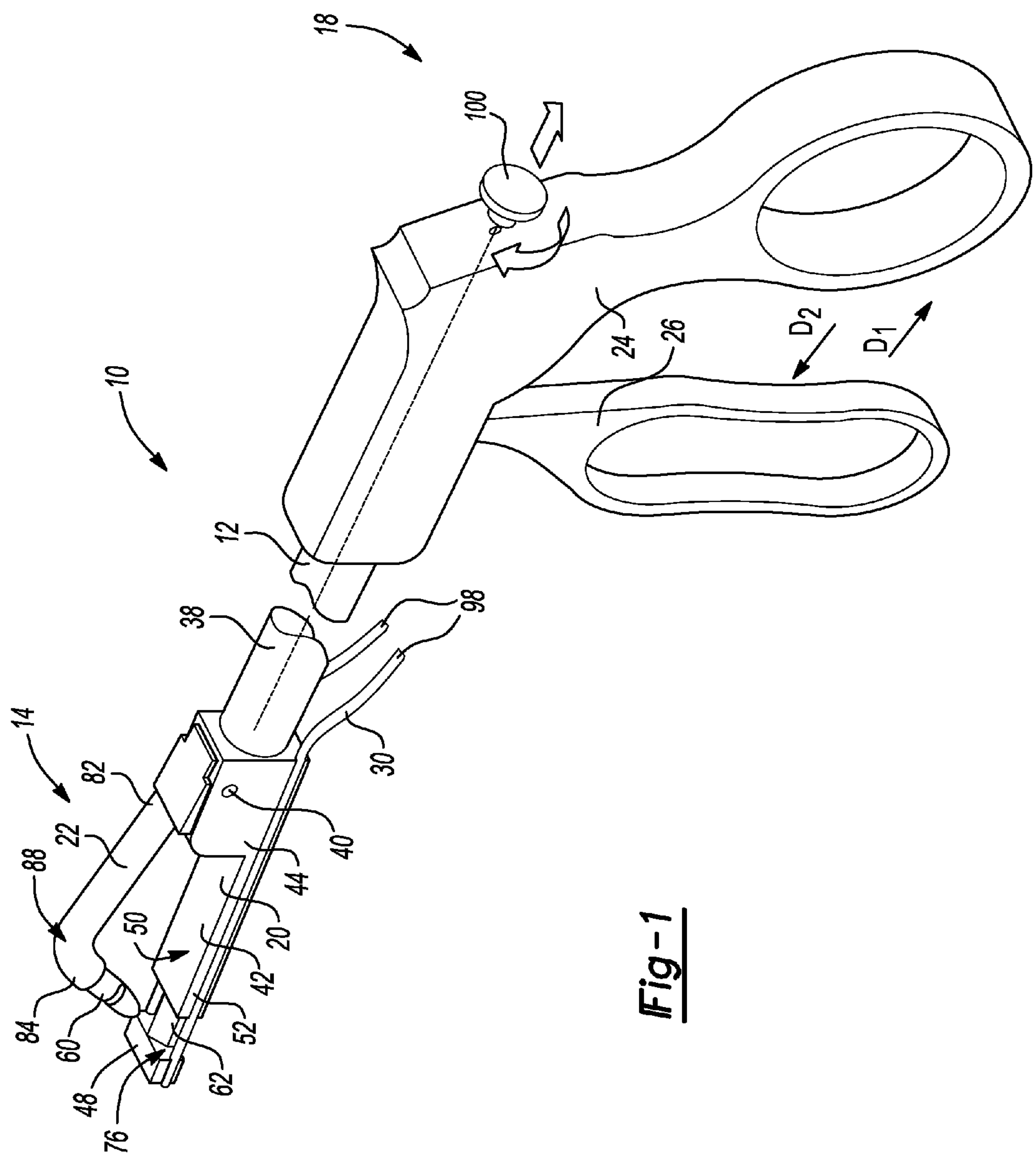
FIG. 1 is a perspective view of an apparatus for passing suture through tissue according to the present teachings.
Figure 2:
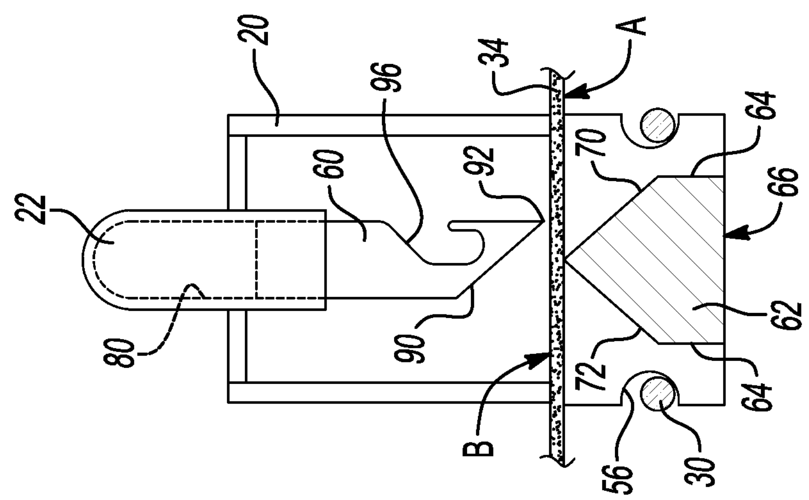
FIG. 2 is a cross-sectional view of the apparatus of FIG. 1 shown with a jaw portion positioned relative to tissue prior to penetration.

With particular reference to FIGS. 1 and 2, the first jaw member 20 will be described in greater detail. The first jaw member 20 generally includes a body portion 42 having a proximal end portion 44 coupled to the second jaw member 22 and a distal end portion 48 extending at an opposite end. The proximal and distal end portions 44 and 48 define an upper face 50 opposing the second jaw 22, a lower face (not specifically shown) and a sidewall 52 extending between the upper face 50 and the lower face. The proximal and distal end portions 44 and 48 collectively define a retaining structure around the respective sidewall 52 in the form of a groove 56 (FIG. 2). The groove 56 is operable to locate a length of the suture 30 in a position to be captured by a needle 60 extending from the second jaw 22 during a surgical procedure. The body portion 42 is further defined by an intermediate bridge portion 62 extending between the proximal and distal end portions 44 and 48. The bridge portion 62 includes opposite sidewalls 64, a lower face 66 and a first and second angled engaging surfaces 70 and 72. The bridge portion 62 is positioned inboard relative to the sidewall 52 and groove 56 of the body 42 forming a stepped in portion 76 (FIG. 1) to accommodate the needle 60 during operation as will be described in detail.

With reference now to FIGS. 1-4, the second jaw member 22 will be described in greater detail. The second jaw member 22 includes a barrel portion 80 (FIG. 2) extending from a proximal end 82 at the pivot joint 40 to a distal end 84 having the needle 60 removably received therein. The barrel portion 80 includes an intermediate curved portion 88 (FIG. 1) for locating the needle 60 at an orientation suitable to slidably engage the bridge portion 62 while passing between the bridge portion 62 and the suture 30 during actuation. The needle 60 includes a complementary angled engagement surface 90 for slidably communicating with the first angled engagement surface 70 of the bridge 62. The needle 60 forms a sharp point 92 on a first end for piercing the tissue 34 during a procedure. The needle 60 further defines a hook 96 formed therein. The hook 96 is operable to capture a portion of the suture 30 and draw the portion of suture 30 through the pierced hole 32 formed by the needle 60.

With continued reference to FIGS. 1-4, the operation of the apparatus 10 will be described according to a first method of operation. At the outset, a length of suture 30 is selected for the subject application. The suture 30 is wrapped around the body 42 of the first jaw member 20 in a nesting relationship with the groove 56. Opposite free ends 98 extend away from the first jaw member 20 alongside the longitudinal shaft 12 and may be held taught by the surgeon. It is appreciated that the free ends 98 may be located into a secure position by other methods including retaining structure incorporated on the longitudinal shaft 12, handle portions 24, 26 or elsewhere on the apparatus 10.

Once the suture 30 is located with respect to the first jaw member 20, the jaw end 14 of the apparatus 10 is positioned relative to the tissue 30. Specifically, the first jaw member 20 is located alongside a first surface A of the tissue 34 such that the first surface A of tissue 34 faces the upper face 50 of the body 42 and a second surface B of tissue 34 faces the second jaw member 22. Next, referring to FIG. 2, the jaw end 14 is negotiated into a desired alignment with the tissue 34 to align the needle 60 with a desired piercing point on the tissue 34. Once the alignment is verified, the surgeon actuates the second handle 26 relative to the first handle 24 on the handle end 18 of the apparatus 10. Movement of the second handle 26 in a first direction $D_1$ causes the rod to translate within the tubular portion 38 of the longitudinal shaft 12. Linear translation of the rod imparts rotational movement of the second jaw member 22 about the pivot joint 40 (in a counterclockwise direction as viewed by FIG. 1).

Figure 3:
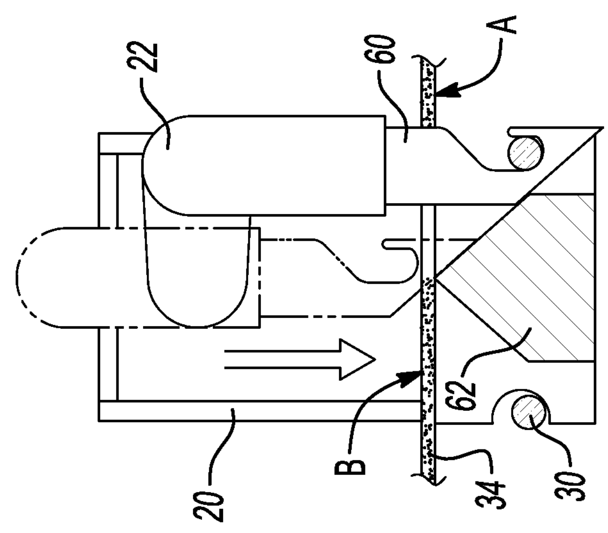
FIG. 3 is a cross-sectional view of the jaw portion of FIG. 2 shown advancing through the tissue during actuation.

With particular reference to FIG. 3, as the second jaw member 22 rotates about the pivot joint 40, the needle 60 penetrates and advances through the tissue 34. While the needle 60 progresses through the tissue 34, the angled engagement surface 90 of the needle 60 slidably advances along the first angled engagement surface 70 of the bridge 62. The slidable communication of the needle 60 along the angled engagement surface 70 of the bridge 62 causes the needle 60 to progressively deflect outwardly with respect to a longitudinal axis of the first jaw member 20. The deflection is facilitated by the flexible nature of the second jaw member 22. The second jaw member 22 may be made of any suitable flexible resilient material such as plastic, rubber, metal, etc., for example.

Upon progressive actuation of the second jaw member 22, the needle 60 passes through the stepped in portion 76 (FIG. 1) and deflects into engagement with a portion of the suture 30. While the second jaw member has been described as having flexible material properties facilitating the deflection of the needle 60, it is appreciated that other mechanical or material configurations may be employed. For example, a pivot joint may be incorporated to provide rotation of the second jaw member 22 about a longitudinal axis defined by the proximal end 82.

Deflection of the needle 60 allows the hook 96 to come into contact and capture a portion of the suture 30. Next, with reference to FIGS. 1-4, the second handle 26 is actuated in a second direction $D_2$ allowing the second jaw member 22 to be retracted from the tissue 34 and pass the portion of suture 30 from the first surface A, through the hole 32 formed in the tissue 34 and to the second surface B. During retraction of the second jaw member 22, the suture 30 is guided along the groove 56 in a direction toward the retracting needle 60.

At this point, the surgeon has a looped portion of suture 30 extending away from the second surface B of tissue 34 and a pair of free ends extending away from the first surface A. The surgeon may then utilize the suture 30 in any desired manner for a given application. For example, the suture 30 may be cut at the looped portion and tied off, or one of the suture ends 98 (FIG. 1) may alternatively be pulled through the hole 32 such that a continuous strand extends through the tissue 34.

With reference now to FIGS. 5-10, operation of the apparatus 10 will be described according to a second configuration. In the second configuration, the second jaw member 22 is fixed at the pivot joint 40. A knob 100 (FIG. 1) is operably interconnected to the needle 60 (such as by way of a wire or shaft). The knob 100 may be pulled in a direction away from the first handle 24 to urge the needle 60 to retract into the distal end 84 of the second jaw 22. Likewise the knob 100 may be pushed toward the first handle 24 to urge the needle 60 to advance from the distal end 84 of the second jaw 22. Rotation of the knob 100 influences axial rotation of the needle 60. It is appreciated that the knob 100, may comprise other configurations and/or be located elsewhere on the apparatus 10.

Figure 7:
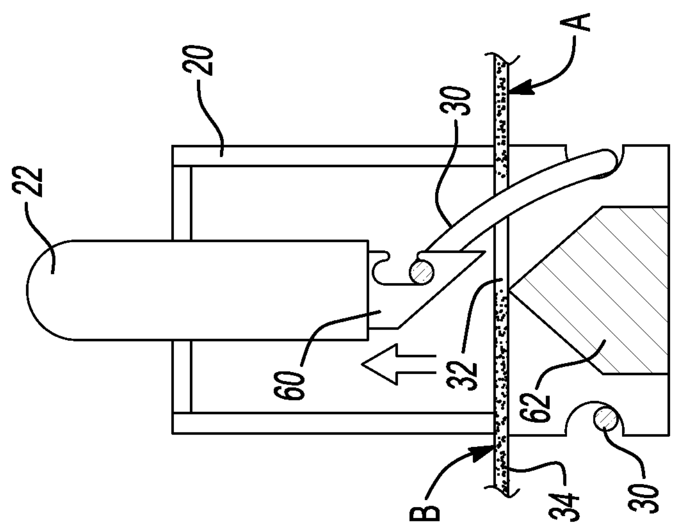
FIG. 7 is a cross-sectional view of the needle portion of FIGS. 6A and 6B shown with a captured portion of suture during retraction from the tissue.
Figure 6A:
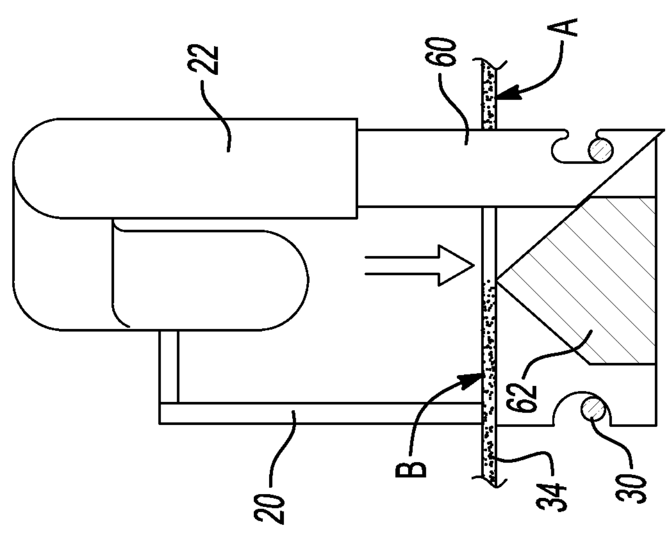
FIG. 6A is a cross-sectional view of the needle portion of FIG. 5 shown advancing though the tissue during actuation according to a first configuration.
Figure 5:
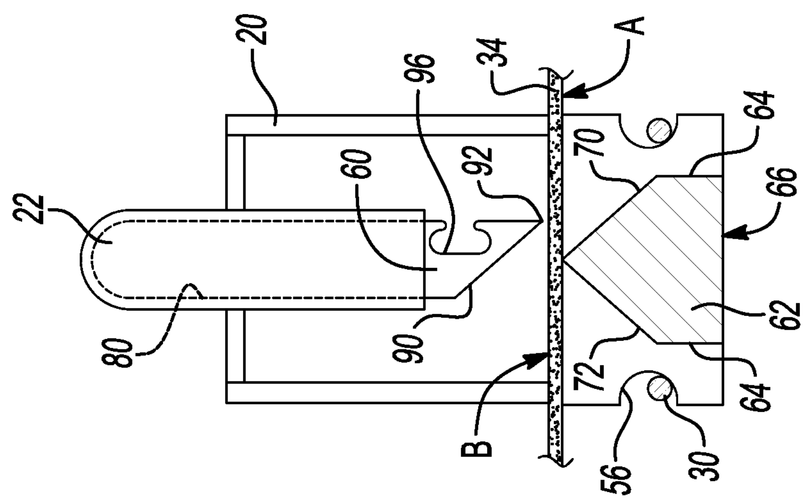
FIG. 5 is a cross-sectional view of the apparatus for passing suture through tissue according to a second configuration.

During operation, linear advancement of the knob 100 causes linear actuation of the needle 60 relative to the distal end 84 of the second jaw member 22. Advancement of the needle 60 causes the needle 60 to pierce through the tissue 34. The needle 60 negotiates along the first angled engaging surface 70 and captures a first portion of suture (FIG. 6A). The needle 60 is next retracted through the tissue 34 (FIG. 7).

Figure 10:
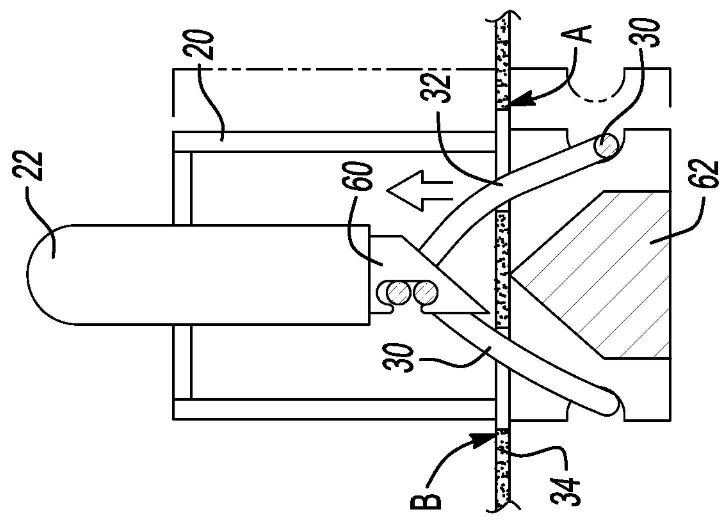
FIG. 10 is a cross-sectional view of the needle of FIGS. 9A and 9B shown with a captured first and second portion of suture during retraction from the tissue.
Figure 8:
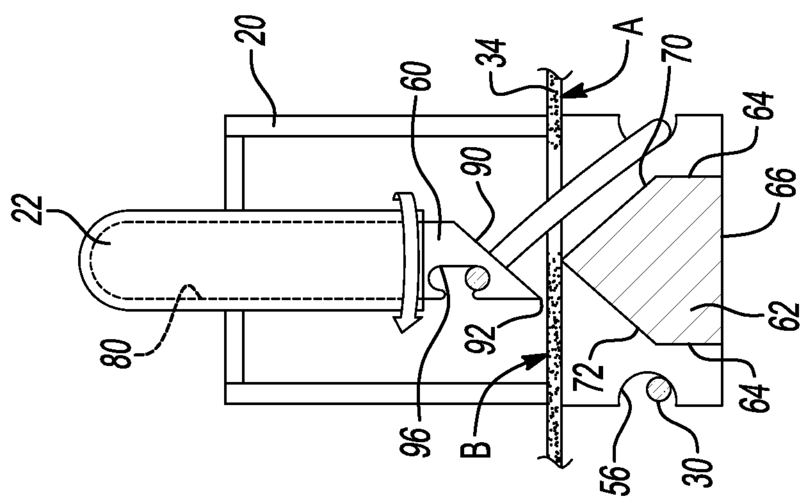
FIG. 8 is a cross-sectional view of the needle portion of FIG. 7 shown rotated 180 degrees.

At this point, the knob 100 is rotated until the needle 60 rotates approximately 180 degrees (FIG. 8). Next, the apparatus 10 is shifted along the tissue 34 according to the span of suture 30 desired between adjacent holes (FIG. 9A). The needle 60 is advanced through the tissue 34 and negotiated along the second angled engaging surface 72 to capture a second portion of the suture 30. The needle 60, having captured two portions of suture is then retracted through the tissue 34 by pulling the knob 100 (FIG. 10).

Figure 9B:
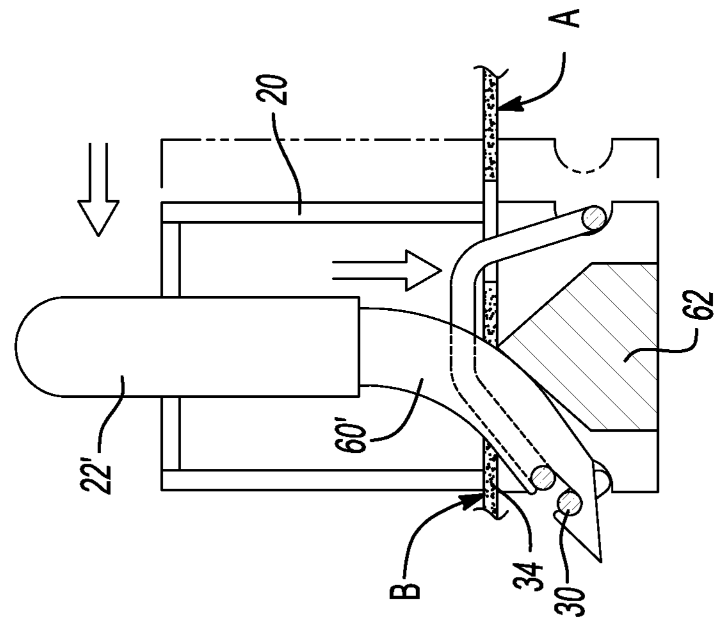
FIG. 9B is a cross-sectional view of the needle of FIG. 8 shown advancing through the tissue according to a second configuration.
Figure 6B:
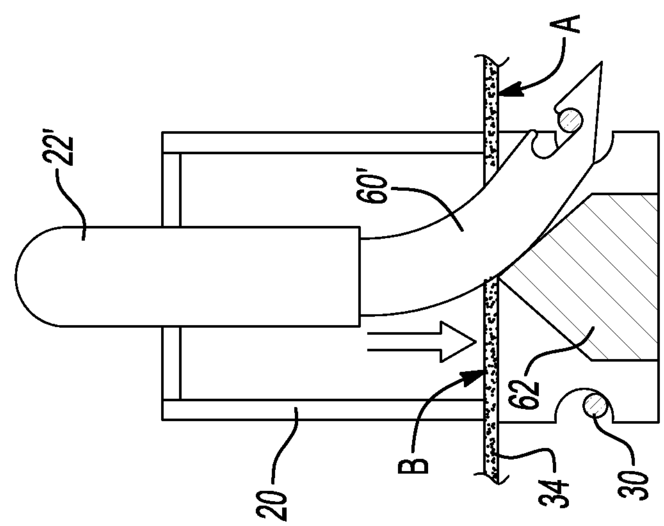
FIG. 6B is a cross-sectional view of the needle portion of FIG. 5 shown advancing through the tissue during actuation according to a second configuration.
Figure 9A:
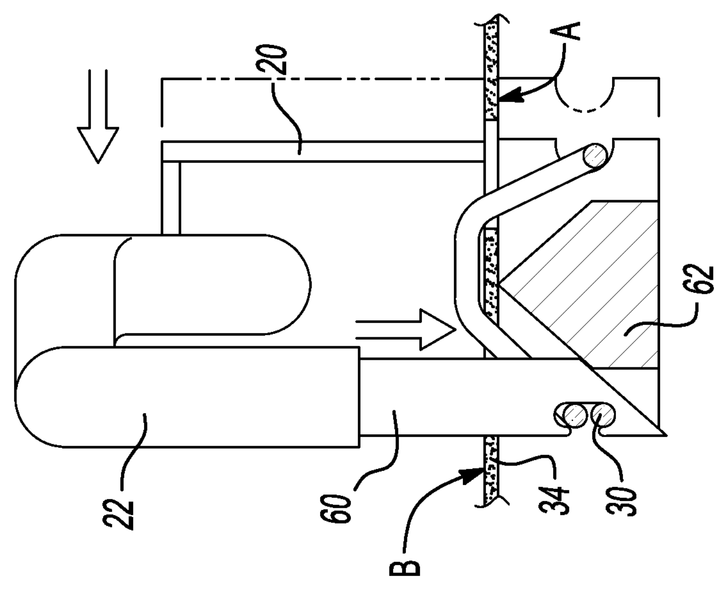
FIG. 9A is a cross-sectional view of the needle of FIG. 8 shown advancing through the tissue according to a first configuration.

In an alternate configuration, as shown in FIGS. 6B and 9B, a second jaw member 22' may comprise a rigid material and a needle 60' may provide flexible material properties. In one example, the needle 60' is made of a nickel-titanium alloy such as nitinol. It is contemplated that in one configuration, both the second jaw member and the needle may provide flexible material properties.

It is appreciated that while the second jaw member 22 is described as fixed in the second configuration, the second jaw member 22 may alternatively be configured to pivot about the pivot joint 40 by translation of the knob 100. In this way, the single needle 60 may be utilized for performing a single stitch and the knob 100 optionally negotiated to rotate the needle 60 for performing a second stitch if desired.

Figure 13:
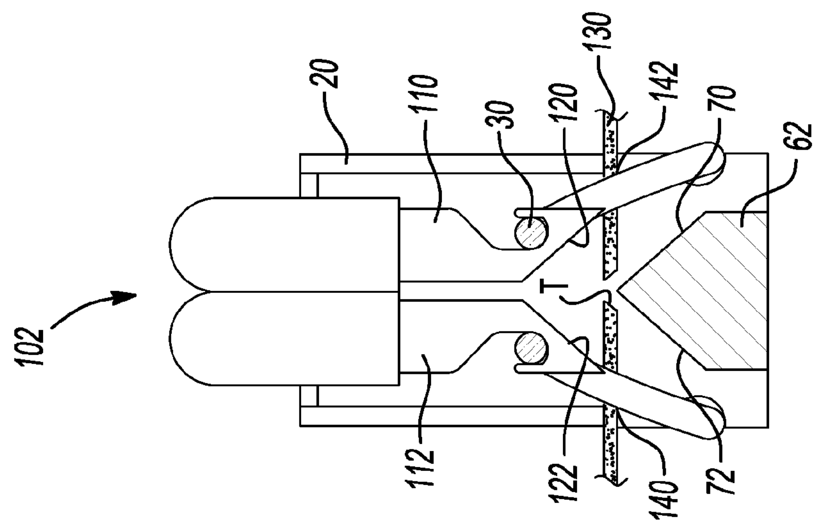
FIG. 13 is a cross-sectional view of the jaw portion of FIG. 12 shown with a captured portion of suture during retraction from the tissue.
Figure 12:
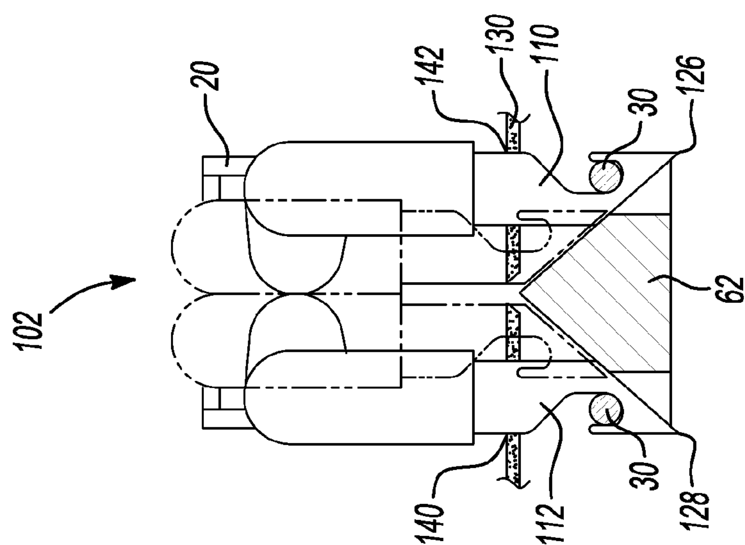
FIG. 12 is a cross-sectional view of the jaw portion of FIG. 11 shown advancing through the tissue during actuation.
Figure 11:
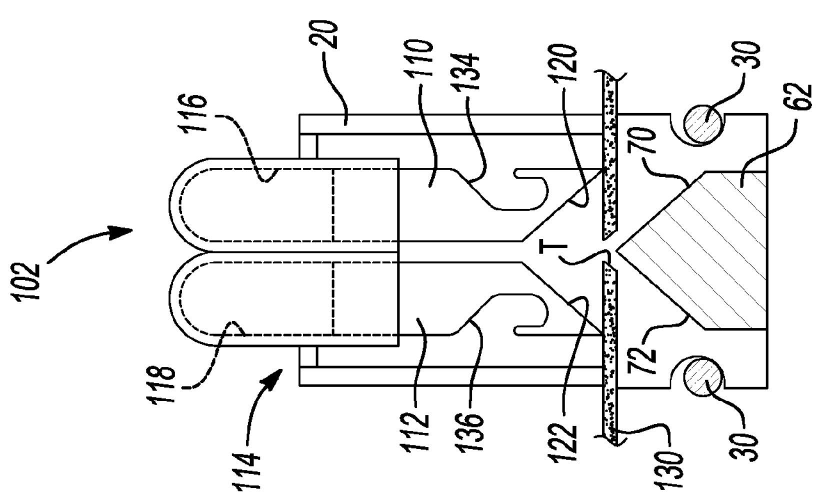
FIG. 11 is a cross-sectional view of a jaw portion according to additional features.

With reference now to FIGS. 11-13, a second jaw member for passing suture through tissue according to additional features is shown and generally identified at reference 102. The second jaw member 102 includes a pair of needles 110, 112 extending from a distal end 114. As will be described, this configuration is particularly useful for performing a mattress stitch.

For clarity, similar reference numbers are used to designate similar components. More specifically, the first jaw member, elongated shaft and handle portion are essentially the same as depicted and explained with respect to FIGS. 1-4. In this regard, it is contemplated that the respective second jaw members 22, 102 may be easily swapped at the pivot joint 40 to provide a different stitch according to the desired application. While the following description is directed to a distinct second jaw member 102 having a pair of needles 110, 112, it is appreciated that alternatively, the second jaw member 22 may remain attached to the apparatus 10 and extend in an offset position (such as to present needle 110 as depicted in FIG. 11). As a result, instead of removing a single assembly barrel and needle to insert a double barrel and needle assembly, a surgeon would leave the single barrel and needle attached and add a second barrel and needle when a mattress stitch is desired. In another variation, a double barrel configuration (FIG. 11) may be provided as the sole second jaw member. In this configuration, a surgeon may remove one of the needles 110, 112 from the double barrel configuration when a single stitch is desired.

The second jaw member 102 will now be described in greater detail. The second jaw member 102 includes a pair of barrel portions 116, 118 at a distal end 114. The pair of barrel portions 116 and 118 are each adapted to accept respective needles 110 and 112 therein. Each needle 110 and 112 includes a complementary angled engagement surface 120, 122 for slidably communicating with the respective first and second angled engagement surfaces 70 and 72 of the bridge 62. Each needle 110 and 112 forms a sharp point 126 and 128 for piercing tissue 130 during a procedure and includes a hook 134 and 136 for capturing a respective portion of the suture 30 and drawing it through each pierced hole 140 and 142 respectively.

In the pictoral representation shown in FIGS. 11-13, the second jaw member 102 is particularly useful for bridging a tear T in the tissue 130. It is appreciated however that the apparatus may be used in other applications for different tissue arrangements. During operation, actuation of the second handle 26 imparts rotational movement of the second jaw member 102 as described above. As the second jaw member 102 rotates about the pivot joint 40, each needle 110 and 112 concurrently penetrates and advances through the tissue 130. While the needles 110 and 112 progress through the tissue (FIGS. 11-12), the respective angled engagement surfaces 120 and 122 of the needles 110 and 112 slidably advance along the first and second engagement surface 70 and 72 of the bridge 62. The slidable communication of the needles 110 and 112 along the angled engagement surfaces 70 and 72 of the bridge 62 causes each needle 110 and 112 to progressively deflect outwardly (away from each other) with respect to a longitudinal axis of the first jaw member 20. The needles 110 and 112 pass into engagement with respective portions of the suture 30. Deflection of the needles 110 and 112 allows hooks 134 and 136 to come into contact and capture portions of the suture 30. Retraction of the second jaw member 102 (FIG. 13) allows a pair of looped portions of suture 30 to be drawn through respective holes 140 and 142 in the tissue 130.

At this point, the surgeon may pull each end 98 through the tissue 130 whereby they may be tied or secured according to the desired application. As shown in FIG. 13, a first portion of the suture 30 extends out of the first hole 140 and a second portion extends out of the second hole 142. An intermediate portion of suture 30 (from the portion looped around the distal end 48 of the first jaw member 20) may be drawn toward the tissue 130 to bridge a distance between the first and second holes 140 and 142.

Figures 14, 15, 16:
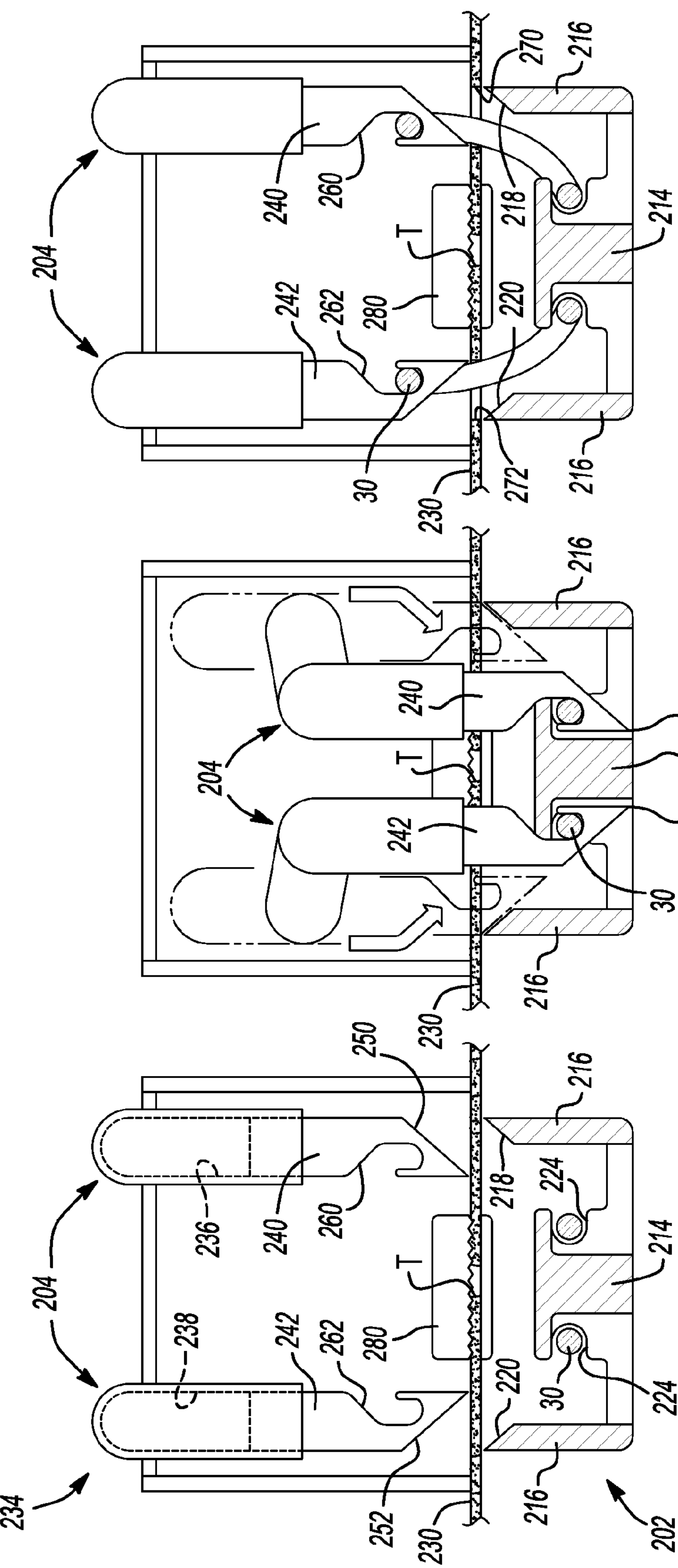
FIG. 14 is a cross-sectional view of a jaw portion according to additional features.
FIG. 15 is a cross-sectional view of the jaw portion of FIG. 14 shown advancing through the tissue during actuation.
FIG. 16 is a cross-sectional view of the jaw portion of FIG. 15 shown with a captured portion of suture during retraction from the tissue.

Turning now to FIGS. 14-16, a first and second jaw member for passing suture through tissue according to additional features are shown and generally identified at reference 202 and 204 respectively. As will be described, the first and second jaw members 202 and 204 cooperate to progressively deflect a pair of needles toward each other after piercing through tissue during a procedure. Such a configuration allows a greater gap between adjacent pierced holes. As a result, a wider suture span may be achieved between adjacent pierced holes. The span of tissue between adjacent pierced holes are suitable to support a length of the suture after performing a selected stitch.

The first jaw member 202 includes a central body portion 214 and outer arm portions 216. The outer arm portions 216 include first and second angled engaging surfaces 218 and 220. The central body portion 214 defines retaining structure in the form of a groove 224 for locating a length of suture 30.

The second jaw member 204 includes a pair of barrel portions 236 and 238 for accepting a pair of needles 240 and 242 therein. Each needle 240 and 242 includes a complementary angled engagement surface 250, 252 for slidably communicating with the first and second angled engagement surfaces 218 and 220 of the arms 216 extending from the first jaw portion 202. Each needle 240 and 242 forms a sharp point 256 and 258 for piercing the tissue 230 during a procedure and includes a hook 260 and 262 for capturing a respective portion of the suture 30 and drawing it through each pierced hole 270 and 272 respectively.

In the pictoral representation shown in FIGS. 14-16, the first and second jaw members 202 and 204 are particularly useful for bridging a tear T in the tissue 230. It is appreciated however that the apparatus may be used in other applications for different tissue arrangements. During operation, actuation of the second handle 26 imparts rotational movement of the second jaw member 204 as described above. As the second jaw member 204 rotates about the pivot joint, each needle 240 and 242 concurrently penetrates and advances through the tissue 230. While the needles 240 and 242 progress through the tissue (FIGS. 14-15), the respective angled engagement surfaces 250 and 252 of the needles 240 and 242 slidably advance along the first and second engagement surfaces 218 and 220 of the arms 216. The slidable communication of the needles 240 and 242 along the angled engagement surfaces 218 and 220 of the arms 216 causes each needle 240 and 242 to progressively deflect inwardly (toward each other) with respect to a longitudinal axis of the first jaw member 202. The needles 240 and 242 pass into engagement with respective portions of the suture 30. Deflection of the needles 240 and 242 allows hooks 260 and 262 to come into contact and capture portions of the suture 30. Retraction of the second jaw member 204 (FIG. 16) allows a pair of looped portions of suture 30 to be drawn through respective holes 270 and 272 in the tissue 230.

At this point, the surgeon may pull each end 98 through the tissue 230 whereby they may be tied or secured according to the desired application. A clamp 280 may additionally be used to clamp a portion of the tissue 230 to the first jaw member 202 if desired during a procedure. As shown in FIG. 16, a first portion of the suture 30 extends out of the first hole 270 and a second portion extends out of the second hole 272. An intermediate portion of suture 30 (from the portion looped around a distal end of the first jaw member 202) may be drawn toward the tissue 230 to bridge a distance between the first and second holes 270 and 272.

While the invention has been described in the specification and illustrated in the drawings with reference to various embodiments, it will be understood by those skilled in the art that various changes may be made and equivalents may be substituted for elements thereof without departing from the scope of the invention as defined in the claims. For example, while the preceding discussion has been particularly directed to passing a suture through tissue, the same may be applied to passing any flexible member through tissue. Likewise, while the second jaw member has been explained as providing rotation, the first jaw member or both jaw members may be operable to provide relative rotation. Furthermore, while configurations explained herein are directed toward a second jaw member having removable needles, the second jaw member may alternatively define integral needle portions. Additionally, while the configurations explained herein have been directed toward manipulating a single strand of suture, it is appreciated that the apparatus 10 may be utilized to manipulate multiple strands of suture either concurrently or sequentially.

Furthermore, the mixing and matching of features, elements and/or functions between various embodiments is expressly contemplated herein so that one of ordinary skill in the art would appreciate from this disclosure that features, elements and/or functions of one embodiment may be incorporated into another embodiment as appropriate, unless described otherwise above. Moreover, many modifications may be made to adapt a particular situation or material to the teachings of the invention without departing from the essential scope thereof. Therefore, it is intended that the invention not be limited to the particular embodiment illustrated by the drawings and described in the specification as the best mode presently contemplated for carrying out this invention, but that the invention will include any embodiments falling within the foregoing description and the appended claims.

What is claimed is:

1. A method for passing a suture through tissue using an instrument having a first jaw member and a second jaw member comprising:

configuring said second jaw member to present a first needle and a second needle, where the second jaw member is capable of performing each of a first distinct stitch and a second distinct stitch;

selecting one of said first stitch and second stitch; and actuating said first and second needles to perform said selected stitch.

2. The method of claim 1 wherein configuring said second jaw member comprises:

assembling the second jaw member defining at least a first barrel with said instrument, said first barrel having said first needle extending therefrom.

3. The method of claim 1 wherein actuating comprises:

translating said first needle to capture a first portion of the suture;

retracting said first needle;

translating said second needle to capture a second portion of the suture; and retracting said second needle.

4. The method of claim 1 wherein configuring said second jaw member comprises:

assembling the second jaw member defining a double barrel with said instrument, said double barrel having said first and second needles extending from respective barrels of said double barrel.

5. The method of claim 4 wherein actuating comprises:

translating said first and second needles to capture a first and second portion of the suture; and retracting said first and second needles having said first and second portion of the suture captured thereto.

6. The method of claim 4 wherein capturing said first and second portion of the suture further includes piercing through the tissue at a first location with said first needle and piercing through the tissue at a second location with said second needle, wherein a distance between said first and second locations defines a span of tissue suitable to support a length of the suture after performing said selected stitch.

7. The method of claim 6 wherein translating said first and second needles includes slidably engaging a first and second angled engagement surface on said first jaw member, whereby said first and second needles deflect toward each other to capture said first and second portion of the suture.

8. The method of claim 1 wherein configuring said second jaw member includes selecting a second jaw member from a plurality of jaw members.

9. The method of claim 1 wherein said first stitch includes a single stitch and said second stitch includes a mattress stitch.

10. A method for passing a suture through tissue using an instrument having a first jaw member and a second jaw member, the first jaw member having a retaining structure to support a portion of the suture, the method comprising, in order, the following;

configuring said second jaw member to accept a first needle and a second needle for performing a stitch;

locating the tissue between the first and second jaw members;

advancing the second jaw member in a first direction toward the tissue whereby said first needle advances through the tissue creating a first pierced hole in the tissue;

advancing the second jaw member in a second direction whereby said first needle captures the supported portion of the suture and draws the suture through said first pierced hole in the tissue; and advancing the second jaw member in the first direction toward the tissue whereby the second needle advances through the tissue creating a second pierced hole in the tissue.

11. The method of claim 10 wherein advancing one of the first and second jaw members in a first direction further comprises:

advancing said second needle through the tissue creating a second pierced hole in the tissue in said second configuration.

12. The method of claim 10 further comprising:

advancing said second needle in a second direction whereby said second needle captures the supported portion of suture and draws the suture through said second pierced hole in the tissue.

13. The method of claim 12 wherein advancing the second jaw member in the second direction comprises:

slidably retracting said first needle across an engagement surface on the first jaw member whereby said first needle progressively deflects inwardly with respect to a longitudinal axis of the first jaw member while drawing the suture through said first pierced hole in the tissue.

14. The method of claim 10 wherein advancing the second jaw member in the first direction comprises:

pivotally rotating the second jaw member relative to the first jaw member.

15. The method of claim 13 wherein pivotally rotating the second jaw member comprises:

rotating the second jaw member relative to the first jaw member whereby said first needle passes between the first jaw member and the suture.

16. The method of claim 10 wherein advancing the second jaw member in the first direction comprises:

slidably advancing said first needle along an engagement surface on the first jaw member whereby said first needle progressively deflects outwardly with respect to a longitudinal axis of the first jaw member and into engagement with the suture upon said advancing.

17. A method for passing a suture through tissue comprising:

positioning the tissue against a first jaw member of an instrument to support the tissue;

slidably advancing along a first engagement surface of the first jaw member a first needle supported by a second jaw member of the instrument that is opposite to the first jaw member to penetrate the tissue with the first needle and create a first hole in the tissue, the first needle penetrates the tissue without the suture hooked thereto;

hooking the first needle to a first suture portion of the suture after the tissue has been penetrated by the first needle;

slidably withdrawing the first needle along the first engagement surface with the first suture portion hooked thereto and pulling the first suture portion through the first hole; and stitching the suture to the tissue with one of a single stitch or a mattress stitch.

18. The method of claim 17, further comprising pivotally rotating the first jaw member relative to the second jaw member to slidably advance the first needle along the first engagement surface and penetrate the tissue to form the first hole.

19. The method of claim 17, further comprising:

slidably advancing along a second engagement surface adjacent to the first engagement surface the first needle with the first suture portion hooked thereto to penetrate the tissue with the first needle and create a second hole in the tissue;

hooking the first needle to a second suture portion of the suture; and slidably withdrawing the first needle along the second engagement surface with both the first suture portion and the second suture portion hooked thereto, and pulling both the first suture portion and the second suture portion through the second hole.

20. The method of claim 17, further comprising:

slidably advancing along a second engagement surface of the first jaw member a second needle supported by the second jaw member to penetrate the tissue with the second needle and create a second hole in the tissue;

hooking the second needle to a second suture portion of the suture; and slidably withdrawing the second needle along the second engagement surface with the second suture portion hooked thereto and pulling the second suture portion through the second hole.

21. A method for passing a suture through tissue using an instrument having a first jaw member and a second jaw member, the first jaw member having a retaining structure to support a portion of the suture, the method comprising:

locating the tissue between the first and the second jaw members;

advancing the second jaw member in a first direction toward the tissue whereby a first needle advances through the tissue creating a first pierced hole in the tissue, the first needle is slidably advanced along a first engagement surface on the first jaw member whereby the first needle progressively deflects outwardly with respect to a longitudinal axis of the first jaw member and into engagement with the suture upon advancing; and advancing the second jaw member in a second direction whereby the first needle captures the supported portion of the suture and draws the suture through the first pierced hole in the tissue, the first needle is slidably retracted across the first engagement surface on the first jaw member whereby said first needle progressively deflects inwardly with respect to the longitudinal axis of the first jaw member while drawing the suture through said first pierced hole in the tissue.

22. The method of claim 21, further comprising:

advancing the second jaw member in the first direction toward the tissue whereby a second needle advances through the tissue creating a second pierced hole in the tissue, the second needle is slidably advanced along a second engagement surface on the first jaw member whereby the second needle progressively deflects outwardly with respect to the longitudinal axis of the first jaw member and into engagement with the suture upon advancing; and advancing the second jaw member in the second direction whereby the second needle captures the supported portion of the suture and draws the suture through the second pierced hole in the tissue, the second needle is slidably retracted across the second engagement surface on the first jaw member whereby the second needle progressively deflects inwardly with respect to the longitudinal axis of the first jaw member while drawing the suture through the second pierced hole in the tissue.

23. The method of claim 21, wherein the second jaw member is advanced in the first direction through the tissue without the suture hooked thereto.

24. The method of claim 22, further comprising:

configuring the second jaw member to accept the first needle for performing a stitch; and configuring the second jaw member to accept the second needle.

* * * * *

UNITED STATES PATENT AND TRADEMARK OFFICE

CERTIFICATE OF CORRECTION

PATENT NO. : 8,444,659 B2
APPLICATION NO. : 12/777704
DATED : May 21, 2013
INVENTOR(S) : Kevin T. Stone et al.

It is certified that error appears in the above-identified patent and that said Letters Patent is hereby corrected as shown below:

In the Specification:

Column 1, line 8, "10/984,608 now U.S. Patent No. 7,722,630 filed" should be --10/984,608, now U.S. Patent No. 7,722,630, filed--.

Column 1, line 54, before "jaw", insert --second--.

Column 2, line 45, "though" should be --through--.

Column 4, line 19, "taught" should be --taut--.

Column 4, line 26, "tissue 30" should be --tissue 34--.

Column 5, line 22, after "jaw" insert --member--.

Column 5, line 24, after "jaw" insert --member--.

Column 6, line 32, "pictoral" should be --pictorial--.

Column 7, line 26, "pictoral" should be --pictorial--.

In the Claims:

Column 9, line 58, Claim 15, delete "claim 13" and insert --claim 14--.

Signed and Sealed this
Seventeenth Day of September, 2013

Teresa Stanek Rea
*Deputy Director of the United States Patent and Trademark Office*

Column 11, lines 24-26, Claim 23, delete "23. The method of claim 21, wherein the second jaw member is advanced in the first direction through the tissue without the suture hooked thereto." and insert --23. The method of claim 22, further comprising:

configuring the second jaw member to accept the first needle for performing a stitch; and configuring the second jaw member to accept the second needle.--

Column 11, lines 27-31, Claim 24, delete "24. The method of claim 22, further comprising:

configuring the second jaw member to accept the first needle for performing a stitch; and configuring the second jaw member to accept the second needle." and insert --24. The method of claim 21, wherein the second jaw member is advanced in the first direction through the tissue without the suture hooked thereto.--